US012733933B2

(12) United States Patent
De Ruiter

(10) Patent No.: US 12,733,933 B2
(45) Date of Patent: Sep. 15, 2026

(54) IMPLANTABLE NEUROMA FORMATION PREVENTING DEVICES

(71) Applicant: G.C.W. DE RUITER HOLDING B.V., Wassenaar (NL)

(72) Inventor: Godard Cornelis Willem De Ruiter, Wassenaar (NL)

(73) Assignee: InNerve8 B.V., Schiedam (NL)

( * ) Notice: Subject to any disclaimer, the term of this patent is extended or adjusted under 35 U.S.C. 154(b) by 504 days.

(21) Appl. No.: 18/555,878

(22) PCT Filed: Apr. 21, 2022

(86) PCT No.: PCT/EP2022/060555

§ 371 (c)(1),
(2) Date: Oct. 18, 2023

(87) PCT Pub. No.: WO2022/223694

PCT Pub. Date: Oct. 27, 2022

(65) Prior Publication Data

US 2024/0197324 A1 Jun. 20, 2024

(30) Foreign Application Priority Data

Apr. 22, 2021 (NL) ...................................... 2028041

(51) Int. Cl.
*A61B 17/11* (2006.01)
*A61B 17/00* (2006.01)

(52) U.S. Cl.
CPC ..... *A61B 17/1128* (2013.01); *A61B 17/00491* (2013.01); *A61B 2017/1132* (2013.01)

(58) Field of Classification Search
CPC .................... A61B 17/1128; A61B 2017/1132
See application file for complete search history.

(56) References Cited

U.S. PATENT DOCUMENTS 3,786,817 A * 1/1974 Palma ................ A61B 17/1128 606/152
3,833,002 A * 9/1974 Palma ................ A61B 17/1128 606/154

(Continued)

FOREIGN PATENT DOCUMENTS

EP 0 591 943 A1 4/1994
WO 2008/029373 A2 3/2008

(Continued)

OTHER PUBLICATIONS

International Search Report and Written Opinion for WO 2022/223694 (PCT/EP2022/060555), dated Sep. 28, 2022, pp. 1-17.

(Continued)

*Primary Examiner* — Colin T. Sakamoto
(74) *Attorney, Agent, or Firm* — Thomas|Horstemeyer, LLP

(57) ABSTRACT

An implantable neuroma formation preventing and/or treatment device configured to prevent formation of and/or treat traumatic neuroma comprises a lower shell member and an upper shell member. The lower shell member is provided with one or two open-topped trenches, each having a receiving section that extends from a respective nerve stump entry port of the device and is configured for placing one mammalian nerve stump therein. Each trench further has an outlet section adjoining the receiving section and configured to receive therein nerve fibres projecting from the nerve stump. The lower shell is also provided with an open-topped and open-loop shaped trench configured to install therein an axonal guiding structure configured to allow for entry of regenerating axons into the axonal guiding structure. The upper shell member is configured to be secured onto the lower shell member, so that the secured upper and lower (Continued)

shell members form a closed shell about the nerve stumps and the axonal guiding structure.

19 Claims, 15 Drawing Sheets

(56) References Cited

U.S. PATENT DOCUMENTS 5,656,605 A * 8/1997 Hansson ................. A61L 31/16 514/8.4
6,716,225 B2 * 4/2004 Li ...................... A61B 17/1128 600/36
7,147,647 B2 * 12/2006 Onyekaba .......... A61B 17/1128 606/152
7,198,799 B2 * 4/2007 Mueller .................. A61L 31/06 623/23.75
7,615,063 B2 * 11/2009 Doi .................... A61B 17/1128 606/152
8,257,372 B2 * 9/2012 Swain ................ A61B 17/1128 606/152
11,109,865 B1 * 9/2021 Horava .............. A61B 17/1128
2010/0023031 A1 * 1/2010 Catalano ............ A61B 17/1128 606/152
2011/0125170 A1 * 5/2011 Hoke ...................... A61L 27/48 156/60
2014/0163587 A1 * 6/2014 Yang .................. A61B 17/1128 606/152

FOREIGN PATENT DOCUMENTS

WO 2019/023274 A1 1/2019
WO 2020/010164 A1 1/2020

OTHER PUBLICATIONS

Search Report for NL 2028041, dated Jan. 11, 2022, pp. 1-3.

Strobel Sandra et al: “Tendon Preparation for Cruciate Ligament Reconstruction”, Using the Semitendinosus and Gracilis Tendons, Dec. 31, 2014 (Dec. 31, 2014), pp. 1-36.

* cited by examiner 142
164
163
180
141
171a
127
145
171b
172b
152
151
128b
125a
128a
172a
170b
120
170a
100

IMPLANTABLE NEUROMA FORMATION PREVENTING DEVICES

CROSS-REFERENCE TO RELATED APPLICATIONS

This application is the National Stage of International Application No. PCT/EP2022/060555, filed Apr. 21, 2022, which claims priority to NL 2028041, filed Apr. 22, 2021, which are entirely incorporated herein by reference.

FIELD OF THE INVENTION

The present invention relates to the prevention and/or treatment of the formation of traumatic neuroma at a nerve stump, e.g. at the tibial nerve and the peroneal nerve after human leg amputation.

Various embodiments of Y-conduit devices for the prevention and treatment of the formation of traumatic neuroma at a mammalian nerve stump are discussed in the article: "*Novel experimental surgical strategy to prevent traumatic neuroma formation by combining a 3D-printed Y-tube with an autograft*", A. Bolleboom et al., Journal of Neurosurgery, Volume 130, 184-196, 2019, available at h 49.3171/20178JNS17276. In this document, the authors present several 3D-printed polyethylene Y-shaped conduits which are used to create a loop using an autograft based on the principle of centro-central anastomosis (CCA). The examples presented were tested for the nerve stump of the sciatic nerve and of the peroneal nerve in an adult female Lewis rat (160-200 g, Charles River). The peroneal nerve graft was used as an autograft.

OBJECT OF THE INVENTION

The present invention aims to provide devices that allow for enhanced practical application of implantable neuroma formation preventing and/or treatment devices, e.g. in view of efforts and/or expertise required for their practical use, in particular for use in a human.

The use and the neurological effects of the inventive devices is generally based on the discussion in the above-mentioned article to which reference is made.

The invention provides an implantable neuroma formation preventing and/or treatment device configured to prevent formation of traumatic neuroma at two mammalian nerve stumps, in particular for use in a human, the device comprising:

- a lower shell member,
- an upper shell member,

SUMMARY OF THE INVENTION wherein the lower shell member is provided with:

- open-topped first and second trenches, each having a receiving section that extends from a respective nerve stump entry port of the device and is configured for placing one mammalian nerve stump therein, wherein each first and second trench further has an outlet section adjoining said receiving section and configured to receive therein nerve fibres projecting from the nerve stump received in the receiving section,
- an open-topped and open-loop shaped third trench having opposed ends that each adjoin to a corresponding outlet section of the first and second trenches, the open-loop shaped third trench being configured to install therein an axonal guiding structure having opposed axon entry faces and being configured to allow for entry of regenerating axons from each outlet section via the respective axon entry face into the axonal guiding structure, e.g. said axonal guiding structure being an autograft, wherein the upper shell member is configured to be secured onto the lower shell member after placing of each of the mammalian nerve stumps in the respective one of the receiving sections and after the installation of the axonal guiding structure in the third trench, so that the secured upper and lower shell members form a closed shell about the nerve stumps and the axonal guiding structure.

The axonal guiding structure can be an autograft or can be man-made, e.g. of a polymeric material, e.g. of a biocompatible and/or biodegradable and/or bio-absorbable material.

The axonal guiding structure may, for example, have an elongated structure, e.g. of porous material, e.g. provided with microchannels over the length thereof.

In an embodiment, e.g. having suitable anatomical dimensions, the inventive device addressed above is of practical use for prevention of the formation of neuroma at both the tibial nerve and the peroneal nerve of a human, e.g. as seen when a leg is amputated.

The lower shell of the device can—in use—be placed in proximity of the nerve stumps with the trenches of the lower shell exposed, preferably facing upwards, and readily accessible to place each of the nerve stumps from above in the receiving section of the respective first and second trench and the axonal guiding structure in the open-looped third trench via the open top of the trench. In use, for example, an adhesive is placed first in one or more of the trenches, wherein the nerve stump(s) and/or axonal guiding structure are placed in contact with the adhesive.

In an embodiment, the open-topped first and second trenches of the lower shell of the device have different cross-sectional areas transverse to the extension of the trench. For example, one open-topped trench, e.g. the first, is configured to receive therein the stump at the peroneal nerve of a human having a first cross-sectional area and the other open-topped trench, e.g. the second, being configured to receive therein the stump at the tibial nerve of a human having a second cross-sectional area that is greater than the first cross-sectional area.

In an embodiment, the two open-topped trenches of the lower shell of the device have different depths relative to a top surface of the lower shell member, preferably also different cross-sectional areas, e.g. one open-topped trench, e.g. the first, being configured to receive therein the stump at the peroneal nerve of a human having a first depth and the other open-topped trench, e.g. the second, being configured to receive therein the stump at the tibial nerve of a human having a second depth that is greater than the first depth.

The invention also provides an implantable neuroma formation preventing and/or treatment device configured to prevent formation of traumatic neuroma at a mammalian nerve stump, the device comprising:

- a lower shell member,
- an upper shell member, wherein the lower shell member is provided with:

- an open-topped Y-shaped trench having a receiving section that extends from a nerve stump entry port of the device and is configured for placing one mammalian nerve stump therein, wherein the Y-shaped trench further has branching outlet sections adjoining said receiving section and each configured to receive therein nerve fibres projecting from the nerve stump received in the receiving section, an open-topped and open-loop shaped trench having opposed ends that each adjoin to a corresponding outlet section, the open-loop shaped trench being configured to install therein an axonal guiding structure having opposed axon entry faces and being configured to allow for entry of regenerating axons from each outlet section via the respective axon entry face into the axonal guiding structure, e.g. said axonal guiding structure being an autograft, wherein the upper shell member is configured to be secured onto the lower shell member after placing of the mammalian nerve stump in the receiving section and after the installation of the axonal guiding structure in the open-loop shaped trench, so that the secured upper and lower shell members form a closed shell about the nerve stump and the axonal guiding structure.

The above-mentioned device is suited for application to treat a single mammalian nerve stump, e.g. of a severed human nerve, e.g. resulting from an accident or an amputation.

Generally, the implanted closed shell shields the nerve stump(s) and axonal guiding structure from surrounding tissue and/or direct pressure, e.g. as long as the shell has not been absorbed in a biodegradable embodiment.

The design of the devices as disclosed herein, for example, allows for an amputation to be performed, e.g. of a part of a leg of a human, and for the implanting of the device as part of the surgical amputation procedure wherein the nerve stump(s) is/are created. This avoids the need for performing dedicated surgery after the amputation wound has healed in order to implant the device to avoid or reduce painful neuroma.

The practical usability of the devices disclosed herein, may allow for implanting thereof by someone else than a microsurgeon, e.g. by the surgeon performing the amputation.

The devices disclosed herein are also deemed of benefit for practical treatment of formed neuroma, e.g. as a result of past injury or amputation.

Below optional and/or preferred details of the dual and single nerve stump treatment devices will be discussed. These features are combinable in various combinations, e.g. as shown and/or discussed herein.

In embodiments, the upper shell is provided on its lower side, which lower side is facing the lower shell when the shell is closed, with trenches mating with the trenches of the lower shell, so that—in use—the nerve stump(s) and the axonal guiding structure are received, seen in cross-sectional view, in part in the trench of the lower shell and in part in the trench of the upper shell.

In embodiments, the secured upper and lower shell members form a closed shell about the nerve stump(s) and the axonal guiding structure and cause a clamping of the one or two nerve stumps treated by the device.

In embodiments, the lower shell member is a unitary lower shell member, e.g. molded or printed, e.g. of biocompatible and/or biodegradable and/or bio-absorbable material.

In embodiments, the upper shell member is a unitary upper shell member, e.g. molded or printed, e.g. of biocompatible and/or biodegradable and/or bio-absorbable material.

In an embodiment, one or both of the lower shell member and the upper shell member is made, at least in part, of a material that is transparent or translucent, e.g. allowing for visual checking the proper installation of the nerve stump(s) and/or axonal guiding structure with the shell in closed condition.

In an embodiment, both the lower and upper shell member are of unitary design. In an alternative embodiment, the lower shell member is of unitary design and the upper shell member is composed of two upper shell member parts, each configured to be secured on a respective portion of the lower shell. For example, one upper shell member part is embodied to overlie the trench with the axonal guiding structure and another upper shell member part being embodied to overlie the one or more other trenches of the device.

In embodiments, the upper shell member and lower shell member are interconnected via a hinge structure, e.g. a living hinge. In embodiments, the shell is configured to provide a stable opened position of the upper shell member relative to the lower shell member, e.g. the stable opened position being provided by corresponding embodiment of the hinge structure. This is, for example, known from plastic flip-top cap hinges.

In embodiments, the lower and upper shells are provided with cooperating snap formations configured to keep the shell closed. For example, the snap formations comprise one or more flexible hook formations.

In embodiments, at least the lower shell member, preferably both the lower and upper shell member, are provided remote from the trenches thereof with one or more suture passages therein that are configured to allow for passing a suture there through to stabilize the location of the shell member(s) relative to the mammal, e.g. to the human leg, e.g. prior to installation of the nerve stump(s) in the trench(es) and/or after closing the shell upon completion of the installation.

In embodiments, at least one of the lower shell member and the upper shell member, preferably only the upper shell member, is provided with at least one injection port, each injection port being distinct from the one or two nerve entry ports of the device and being configured for introduction of a fluid, e.g. a saline solution or an adhesive, into the closed shell by means of a syringe, e.g. the injection port being located in the upper shell member over one of the trenches in the associated lower shell. For example, first a saline solution is introduced via the port and then an adhesive, e.g. a fibrin glue, is introduced to plug the port and contain the saline solution in the closed shell.

For example, an injection port is located, e.g. in the upper shell member, in proximity of the join between the outlet section of a nerve stump receiving trench on the one hand and the end of axons guide receiving trench. This allows to, once the shell has been closed, inject a fluid, e.g. a saline solution, in the space between the nerve stump and the axonal guiding structure, so generally where the axons project from the nerve stump and will grow towards and into the axonal guiding structure.

In embodiments, use is made of a syringe for application of the adhesive, e.g. into the trenches of the lower shell (possibly also of the upper shell when provided with trenches) and/or into the closed shell fluid. For example, use is made of a double-barrel syringe, each barrel filled with a component of an adhesive. For example, use is made of a dispensing device that is connectable to a double-barrel syringe and comprises a static mixer for mixing components of the adhesive each dispensed from a respective barrel of the syringe. For example, the dispensing device has body with a tip end and a channel through the body that extends to the tip, wherein the tip is configured to be introduced into and/or connected with the injection port of the device. The static mixer device can be integrated in the channel.

In embodiments, the trenches of the lower shell have trench walls embodied at least in one or more zones thereof with retention enhancing formations, e.g. bosses and/or ribs, e.g. bulbous bosses or barbs, that, e.g. in combination with an adhesive introduced, e.g. in combination with an adhesive applied beforehand or injected after closing of the shell via an injection port, provide enhanced retention of the nerve stump or axonal guiding structure, e.g. providing resistance against a nerve stump becoming separated from receiving section.

The present invention also relates to a kit comprising a device as described herein and an nerve graft, e.g. autograft, preparation tool that is configured to assist in cutting a nerve graft to be received in the axonal guiding structure trench of the device to a predetermined length.

For example, the preparation tool is configured to receive an autograft and to provide an indication and/or guide for a knife, at a location so as to achieve a cutting of the nerve graft to the predetermined length.

For example, the graft preparation tool is embodied with a cutting board having indicia thereon displaying the predetermined length of the graft to be placed in the axonal guiding structure trench of a device as discussed herein and/or having one of more guides for a knife to cut the nerve graft to the predetermined length. The knife can be a handheld surgical knife.

It is noted that the graft preparation tool may also be used for other situations where a nerve graft of a predetermined length is desired.

In embodiments, the tool comprises a board, e.g. of plastic, on which the nerve graft is to be laid. The board is provided with a linear receiver, e.g. a trench, in which the nerve graft to be made to length is placed. As preferred, the trench has a depth that is smaller than the diameter of the nerve graft, so that the nerve graft protrudes somewhat above the board top surface adjacent the trench.

In embodiments, along the length of the trench, the board is provided with indicia forming a ruler allowing to visualize position(s) where the nerve graft is to be severed in order to obtain the desired length, e.g. corresponding to the design of the devices discussed herein. In embodiments, or in combination herewith, the ruler has indications representing a length matching the length of the graft to be placed in one or both of the devices as discussed herein.

As nerve grafts are commonly slippery and difficult to grasp and retain by hand, the tool, as preferred, is provided with at least one graft retainer member, e.g. two graft retainer members, that are configured to retain the graft relative to the board. For example, at least one retainer member is configured to be held relative to the board at multiple positions along the length of the nerve receiver. For example, at least one retainer member is configured to be fitted onto the board and over a nerve graft already placed in the receiver at various positions along the length of the nerve receiver. For example, the board is provided with one or more elongated snap-fit formations, e.g. a groove and/or a slit and/or a rail, extending along the length of the receiver, which can cooperate with one or more snap-fit formations on the retainer member. In another embodiment, at least one retainer member is slidably held on the board so as to be slidable along the length of the nerve receiver.

Preferably, the tool is provided with two graft retainer members, allowing to retain the nerve graft at two locations along the length thereof ahead of severing the graft at one or two locations, e.g. in proximity to one or both of the retainer members.

For example, as the graft is retained on the board, the cutting to length and possibly other preparatory activities related to the nerve graft, can easily be done remote from the surgical site where possibly the device discussed herein is already placed, with the graft being transported to the site whilst retained on the board. The graft can then be picked from the board and installed in the device as discussed herein.

For example, at least one retainer member equally serves as a guide for a knife when severing the graft, e.g. the retainer member having a side perpendicular to the receiver along which the knife can be moved during the severing.

In embodiments, the board of the tool is provided with parallel knife guide formations, e.g. grooves, that are perpendicular to the receiver, e.g. at positions corresponding to likely cuts of the nerve graft. These formations extend at both sides of the receiver, e.g. also across the receiver, and serve to guide the point of the knife while making the cut. The grooves may be shallow for this purpose, e.g. of a lesser depth than the trench in the board receiving the graft.

In embodiments, the tool is disposable, so for single use only.

In embodiments, the tool is distributed, e.g. packaged, in combination with one of the devices discussed herein, e.g. the board having a ruler and/or parallel knife guide formations tuned to the length of the graft that is to be placed in the device.

In embodiments, a knife is integrated with the tool, e.g. movable mounted to the board.

The present invention also relates to a kit comprising a device having, e.g. in the upper shell member, an injection port for a fluid as described herein, the kit further comprising a dispensing device that is connectable to a syringe filled with an adhesive, e.g. a double barrel syringe, e.g. the dispensing device comprising a static mixer for mixing components of the adhesive each dispensed from a respective barrel of the syringe, e.g. the dispensing device having a tip end configured to introduced into and/or connected with the injection port of the device.

A kit may also combine a device as described herein, a nerve graft preparation tool, and a dispensing device that is connectable to a syringe filled with an adhesive.

The present invention also relates to an implantable neuroma formation preventing and/or treatment device configured to prevent formation of and/or treat traumatic neuroma comprises a lower shell member and an upper shell member. The lower shell member is provided with one or two open-topped trenches, each having a receiving section that extends from a respective nerve stump entry port of the device and is configured for placing one mammalian nerve stump therein. Each trench further has an outlet section adjoining the receiving section and configured to receive therein nerve fibres projecting from the nerve stump. The lower shell is also provided with an open-topped and open-loop shaped trench configured to install therein an axonal guiding structure configured to allow for entry of regenerating axons into the axonal guiding structure. The upper shell member is configured to be secured onto the lower shell member, so that the secured upper and lower shell members form a closed shell about the nerve stumps and the axonal guiding structure.

The present invention also relates to a method to prevent formation of and/or to treat traumatic neuroma at one or two mammalian nerve stumps, e.g. at the tibial nerve and the peroneal nerve of a human, wherein use is made of an implantable device as disclosed herein.

In an embodiment, use is made of a device comprising:

a lower shell member, an upper shell member.

wherein the lower shell member is provided with:

open-topped first and second trenches, each having a receiving section that extends from a respective nerve stump entry port of the device and is configured for placing one mammalian nerve stump therein, wherein each first trench and second trench further has an outlet section adjoining said receiving section and configured to receive therein nerve fibres projecting from the nerve stump received in the receiving section, an open-topped and open-loop shaped third trench having opposed ends that each adjoin to a corresponding outlet section of the first and second trenches, the third trench being configured to install therein an axonal guiding structure having opposed axon entry faces and being configured to allow for entry of regenerating axons from each outlet section via the respective axon entry face into the axonal guiding structure, wherein:

the lower shell is placed in proximity of the nerve stumps with the trenches of the lower shell exposed, preferably facing upwards, the nerve stumps are placed via the open top into the respective first and second trench, e.g. after adhesive being deposited in the trench, the axonal guiding structure, e.g. autograft, is placed via the open top into the open-loop shaped trench, e.g. after adhesive being deposited in this trench, the upper shell is secured onto the lower shell member after placing of each of the mammalian nerve stumps in the respective one of the receiving sections and after the installation of the axonal guiding structure in the open-loop shaped trench, so that the secured upper and lower shell members form a closed shell about the nerve stumps and the axonal guiding structure.

In an embodiment, the upper shell is provided with at least two injection ports, each located in proximity of the join between the outlet section of a nerve stump receiving trench on the one hand and the axonal guiding structure receiving trench. Herein, as preferred, the method involves injecting a fluid, e.g. a saline solution, via the port into the space between the nerve stump and the axonal guiding structure. The port, in embodiments, is the plugged by injecting an adhesive into the port, e.g. after having injected a saline solution.

In another embodiment, use is made of a device comprising:

a lower shell member, an upper shell member, wherein the lower shell member is provided with:

an open-topped Y-shaped trench having a receiving section that extends from a nerve stump entry port of the device and is configured for placing one mammalian nerve stump therein, wherein the Y-shaped trench further has branching outlet sections adjoining said receiving section and each configured to receive therein nerve fibres projecting from the nerve stump received in the receiving section, an open-topped and open-loop shaped trench having opposed ends that each adjoin to a corresponding outlet section, the open-loop shaped trench being configured to install therein an axonal guiding structure having opposed axon entry faces and being configured to allow for entry of regenerating axons from each outlet section via the respective axon entry face into the axonal guiding structure wherein:

the lower shell is placed in proximity of the nerve stump with the trench of the lower shell exposed, preferably facing upwards, the nerve stump is placed via the open top into the trench, e.g. after adhesive being deposited in the trench, the axonal guiding structure, e.g. autograft, is placed via the open top into the open-loop shaped trench, e.g. after adhesive being deposited in this trench, the upper shell is secured onto the lower shell member after placing of each of the mammalian nerve stump in the receiving section and after the installation of the axonal guiding structure in the open-loop shaped trench, so that the secured upper and lower shell members form a closed shell about the nerve stump and the axonal guiding structure.

In an embodiment, the upper shell is provided with an injection port that is located in proximity of the join between the outlet section of a nerve stump receiving trench on the one hand and the axons guiding structure receiving trench. Herein, as preferred, the method involves injecting a fluid, e.g. a saline solution, via the port into the space between the nerve stump and the axonal guiding structure. The port, in embodiments, is the plugged by injecting adhesive into the port, e.g. after having injected a saline solution.

The present invention also relates to a device or a kit as disclosed herein for use in a method for preventing the formation of and/or to treat traumatic neuroma at one or two mammalian nerve stumps, e.g. at the tibial nerve and the peroneal nerve of a human.

The present invention also relates to a nerve graft preparation tool as discussed herein, e.g. for use with a device as discussed herein and/or for use in preparation of a nerve graft to be used for another purpose.

BRIEF DESCRIPTION OF THE DRAWINGS

The invention will now be discussed with reference to the drawings. In the drawings.

DETAILED DESCRIPTION OF EMBODIMENTS

Figure 1:
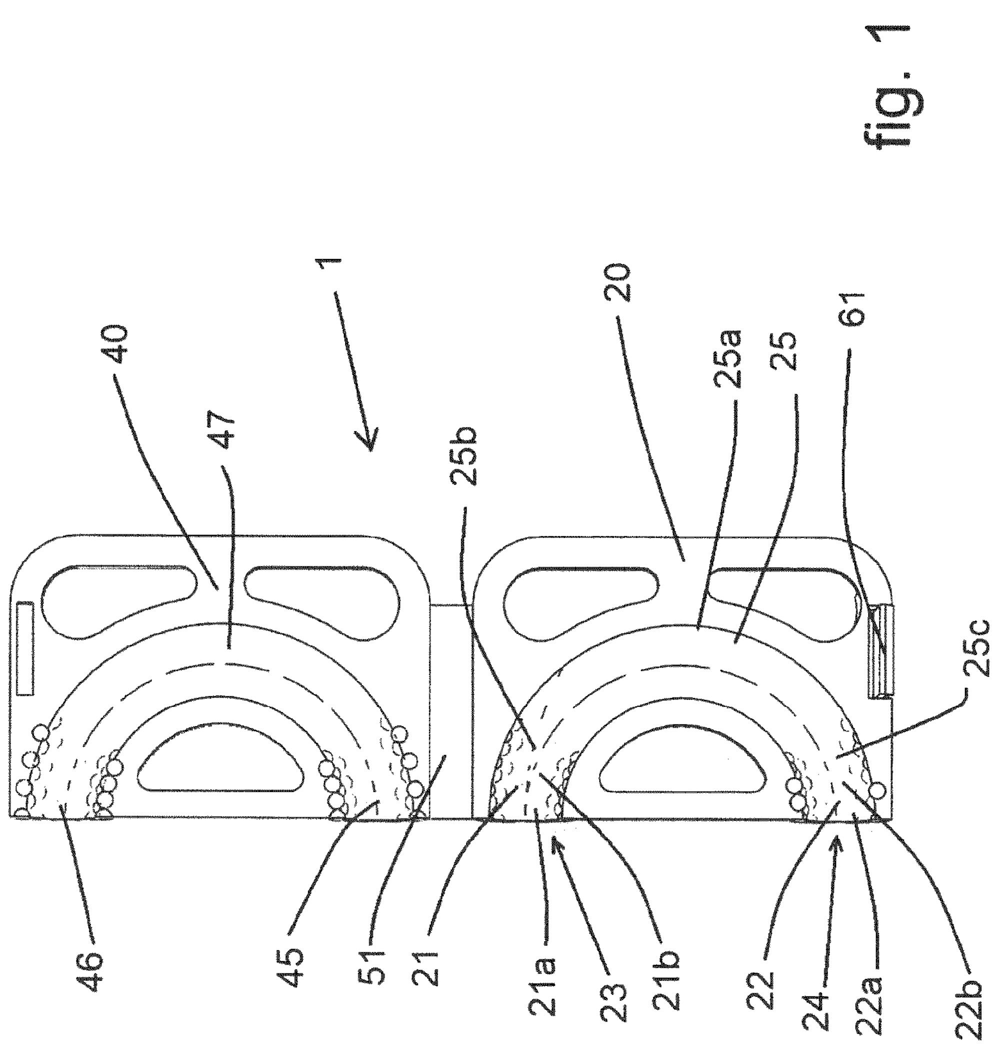
FIG. 1 shows, in a plan view, an exemplary embodiment of a device according to the invention in opened condition.
Figure 2:
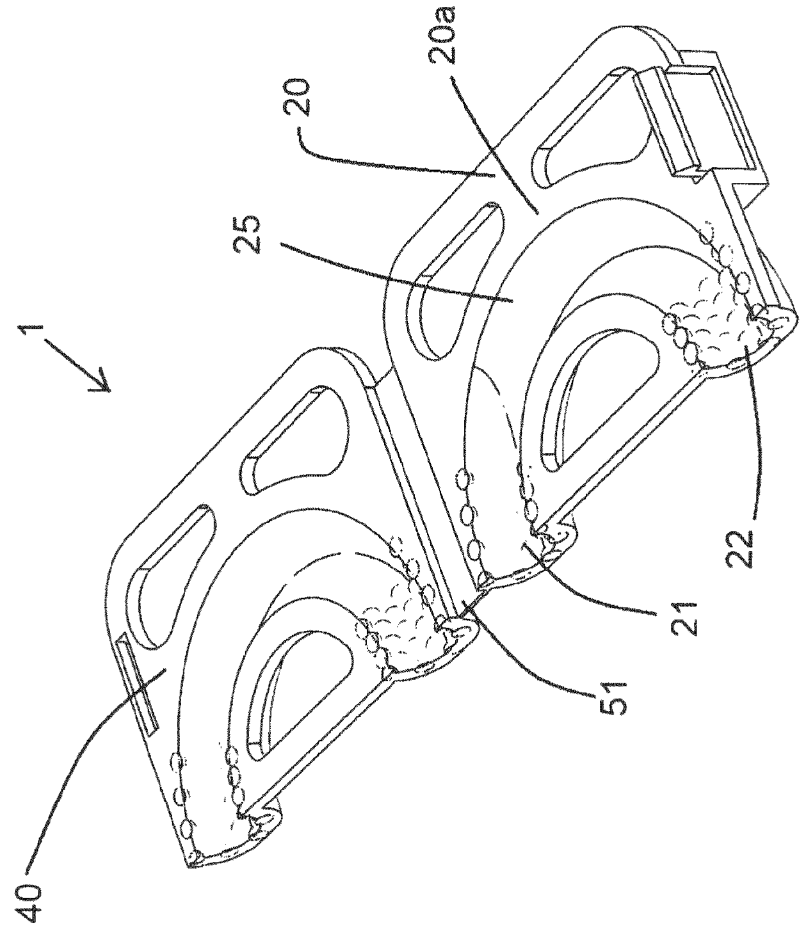
FIG. 2 shows the device of FIG. 1 in a perspective view.
Figure 3:
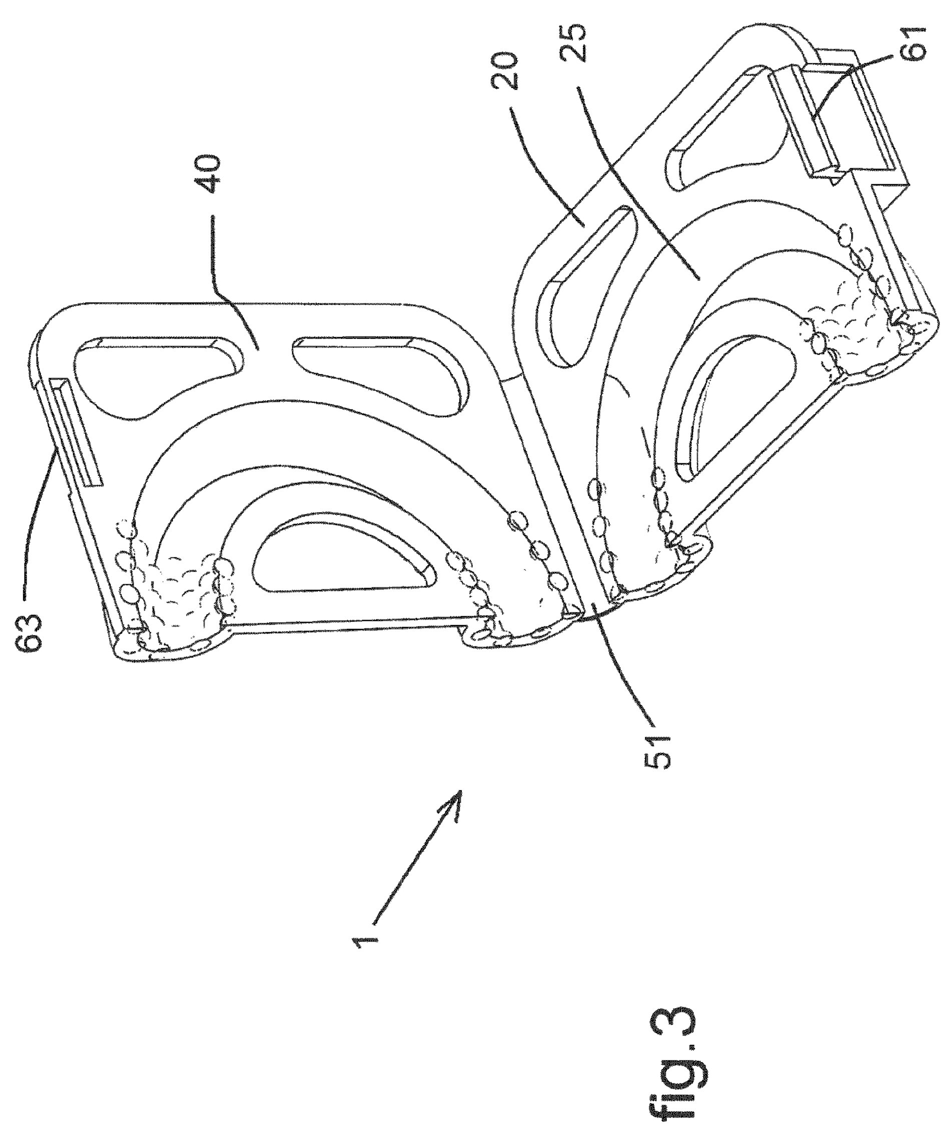
FIG. 3 shows the device of FIG. 1 during closing of the shell.
Figure 4:
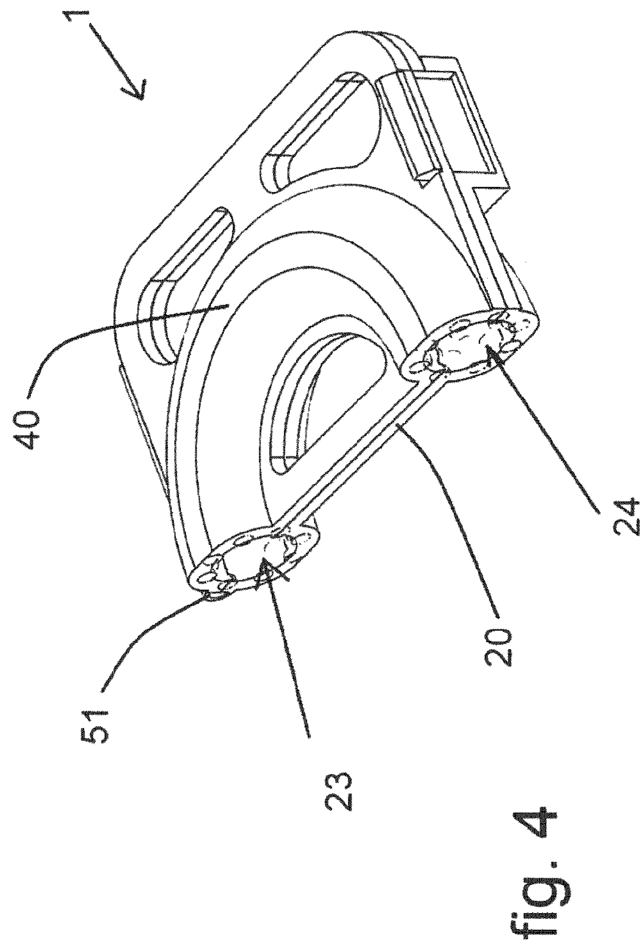
FIG. 4 shows the device of FIG. 1 in closed condition.
Figure 5:
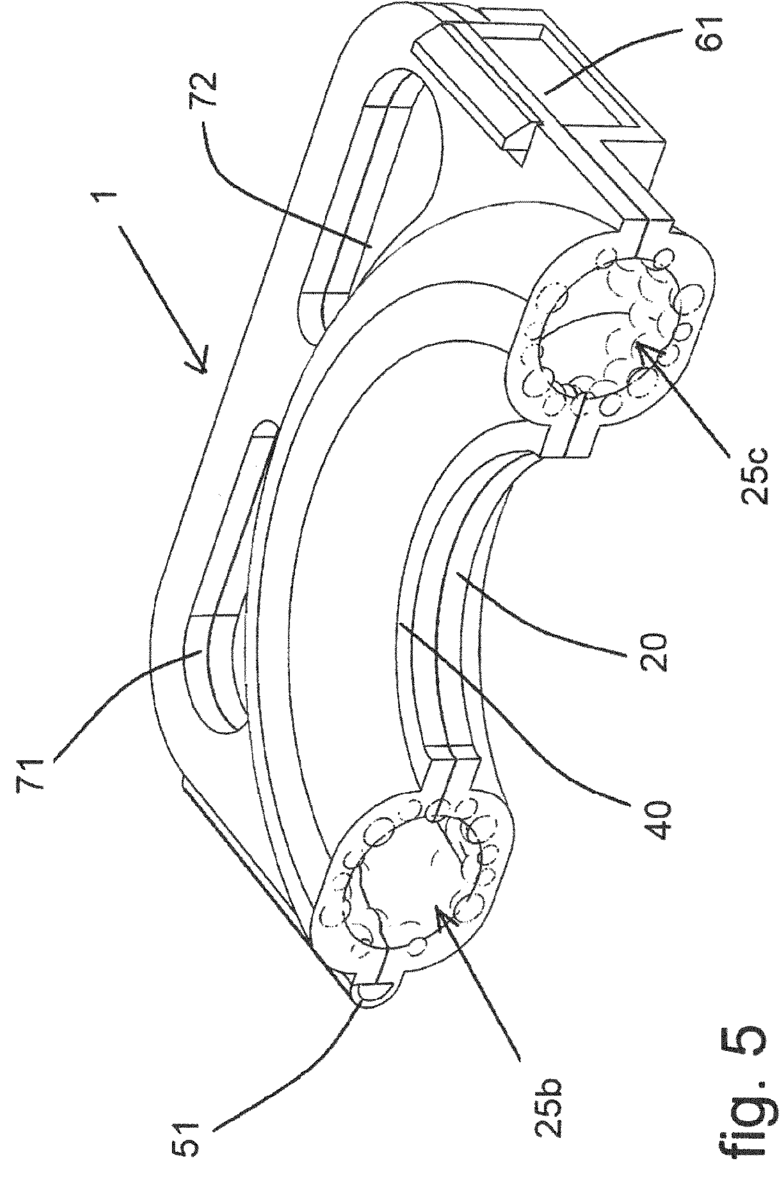
FIG. 5 shows a cross-section of the device in FIG. 5.
Figure 6:
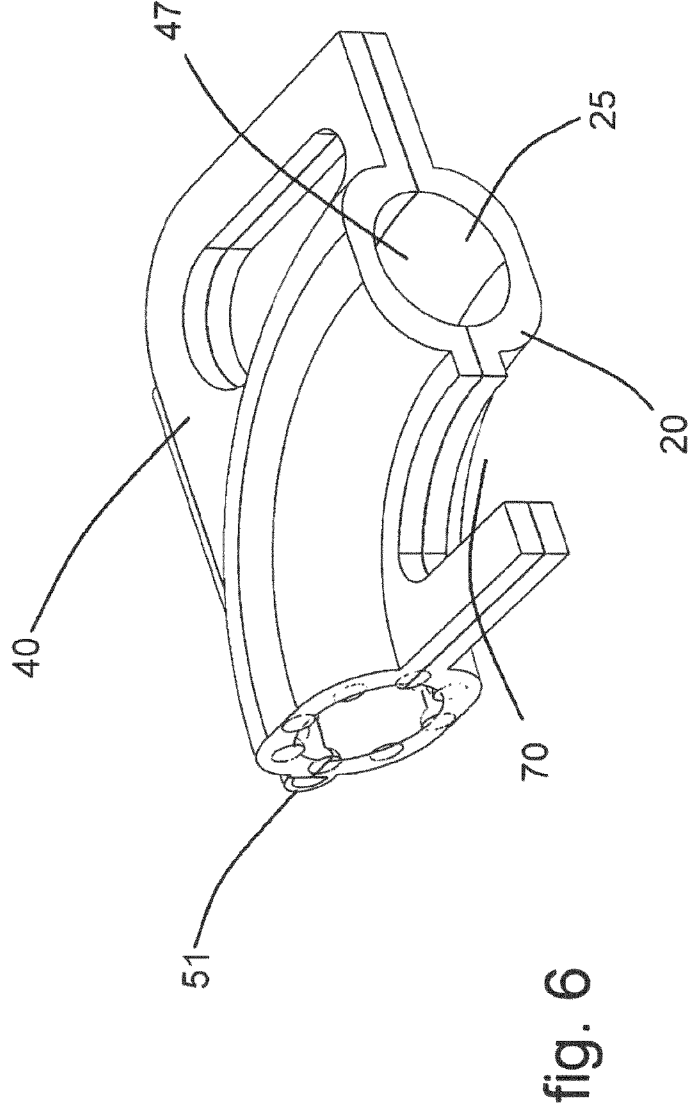
FIG. 6 shows another cross-section of the device in FIG. 5.
Figure 7:
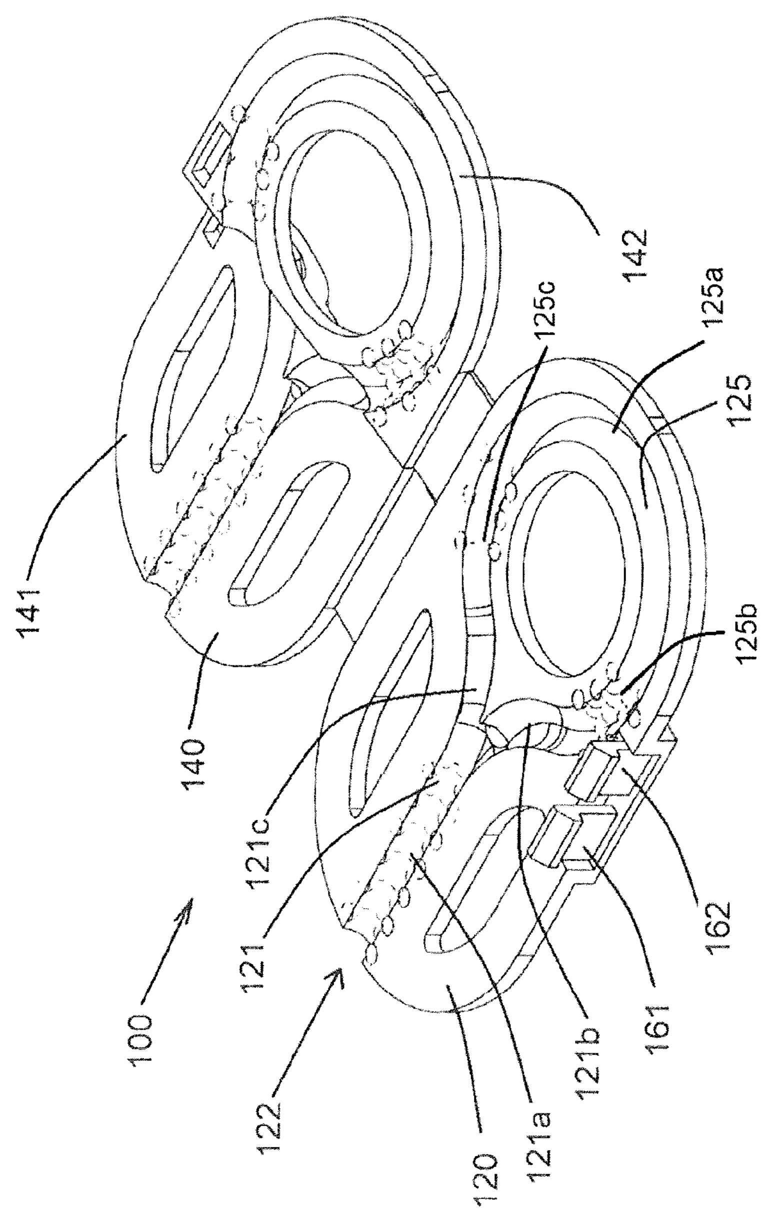
FIG. 7 shows another exemplary device according to the invention in opened condition.
Figure 8:
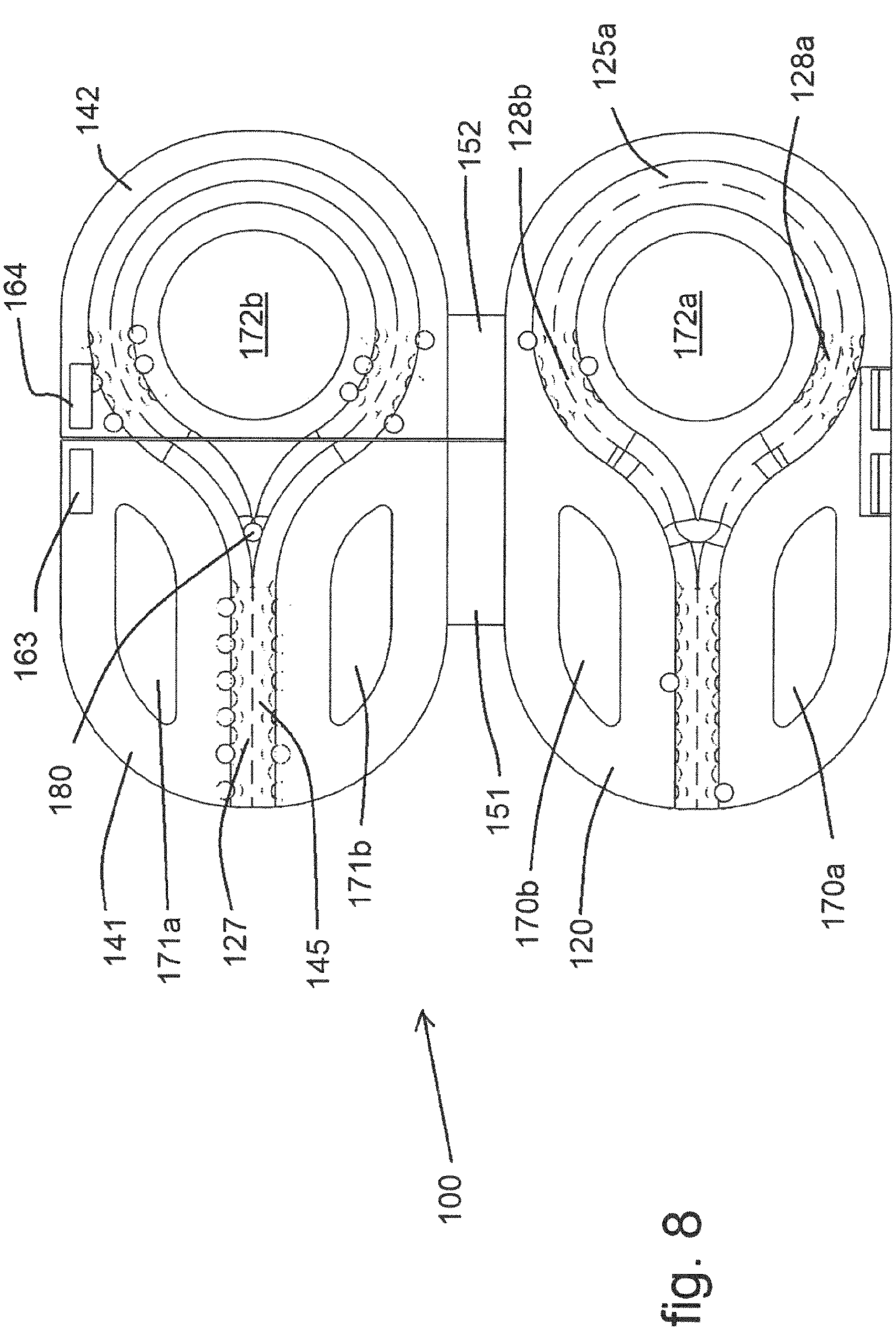
FIG. 8 shows the device of FIG. 7 from above.
Figure 9:
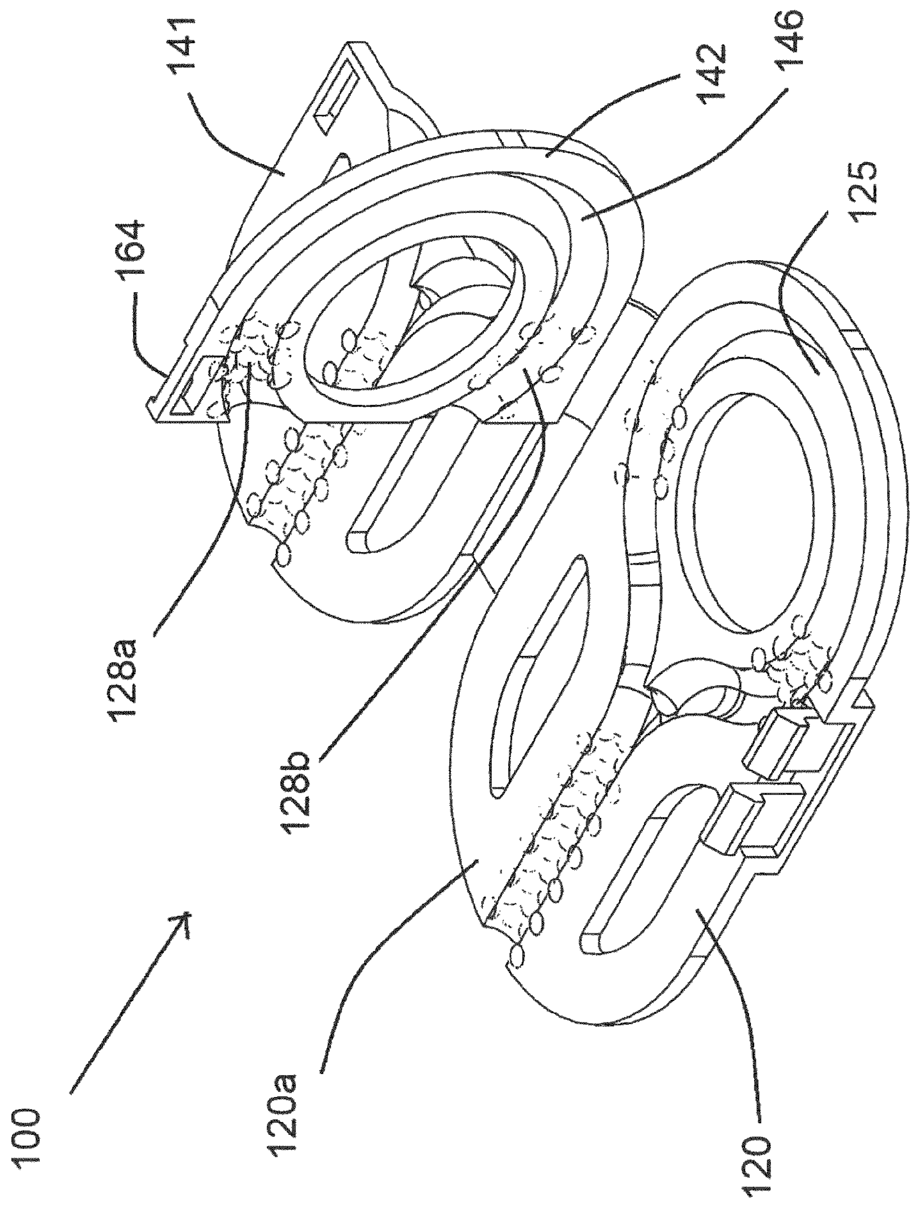
FIG. 9 shows the device of FIG. 7 during closing of a part of the upper shell.
Figure 10:
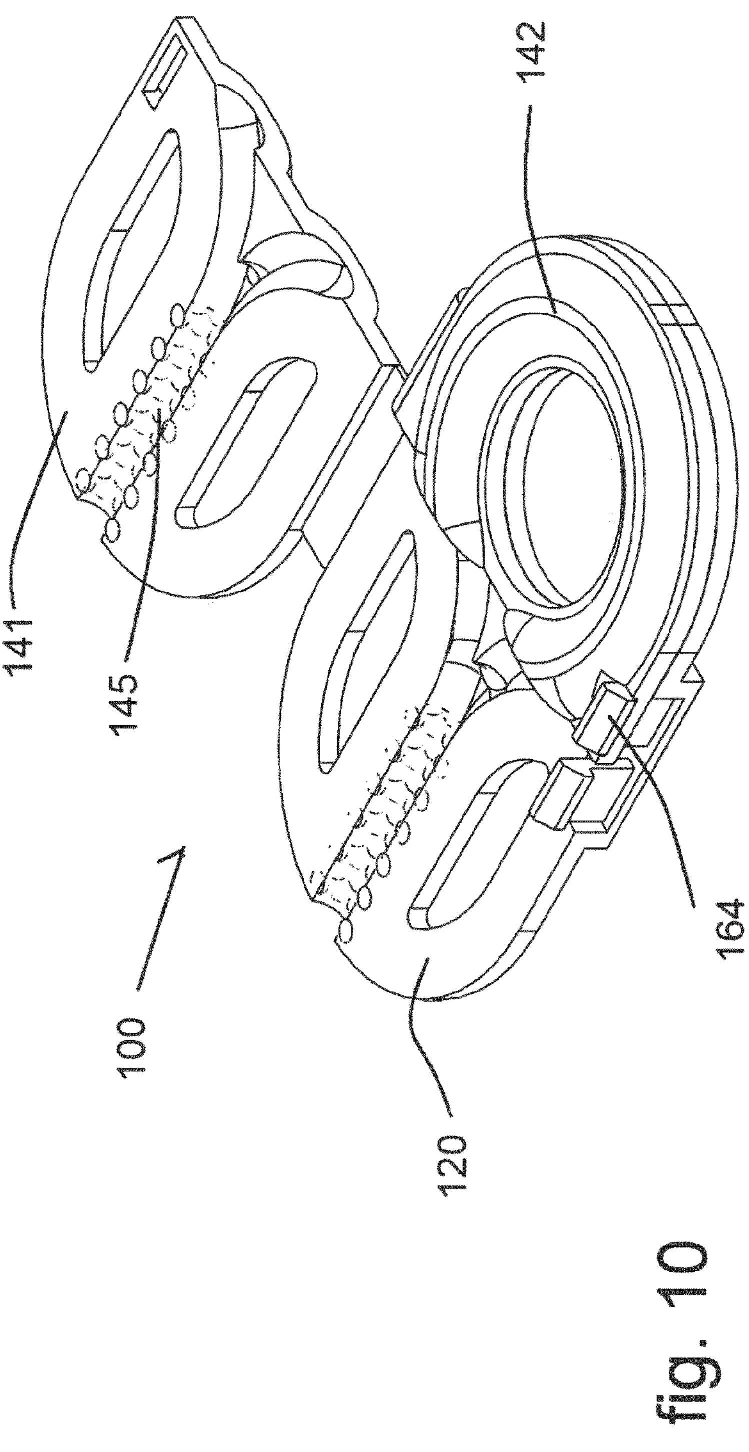
FIG. 10 shows the device when the upper part is in closed condition.
Figure 11:
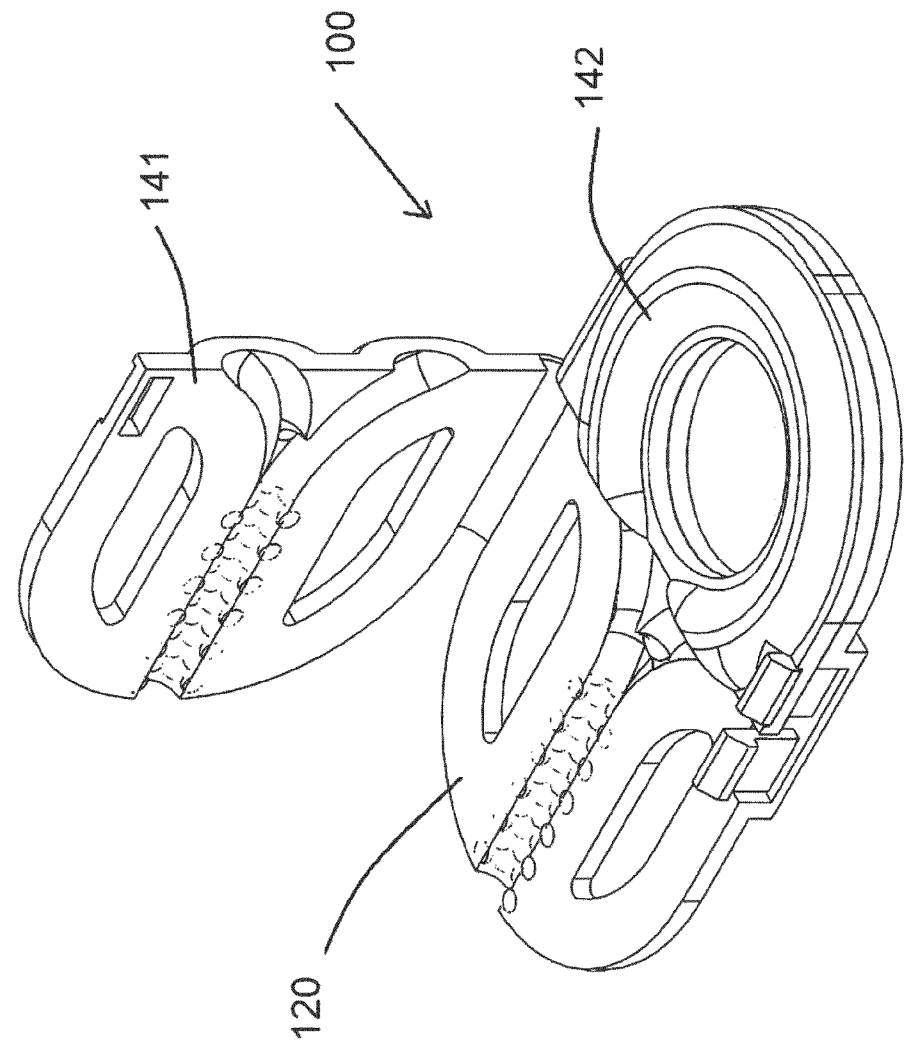
FIG. 11 shows the device of FIG. 10 during closing of the other part of the upper shell.
Figure 12:
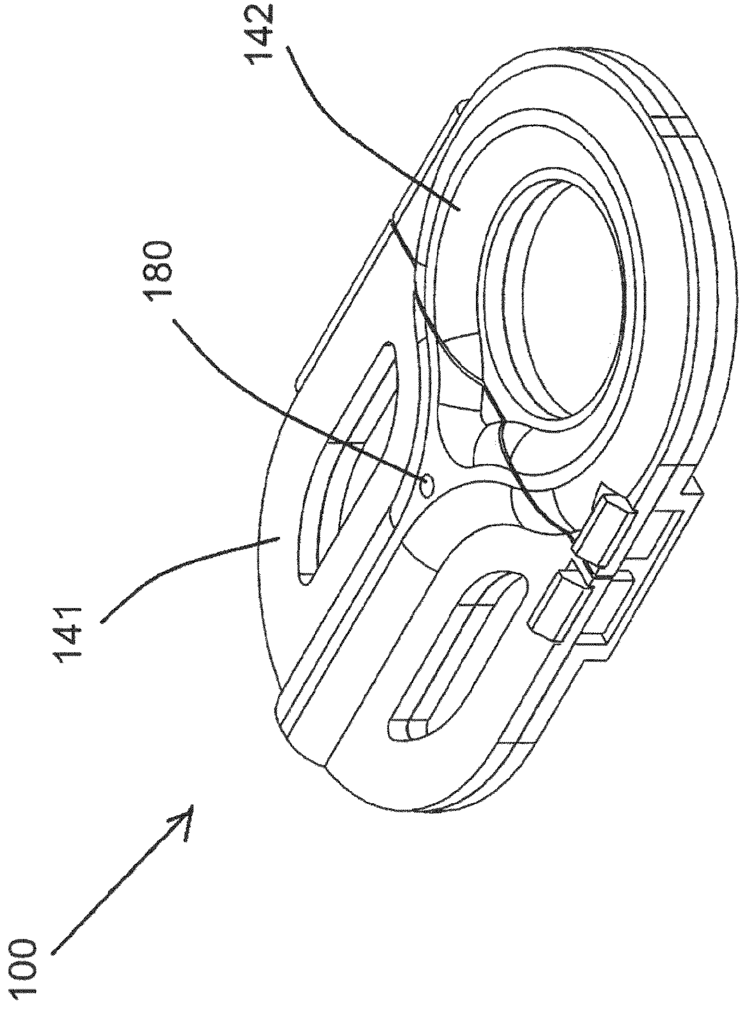
FIG. 12 shows the device of FIG. 7 in the closed condition.
Figure 13:
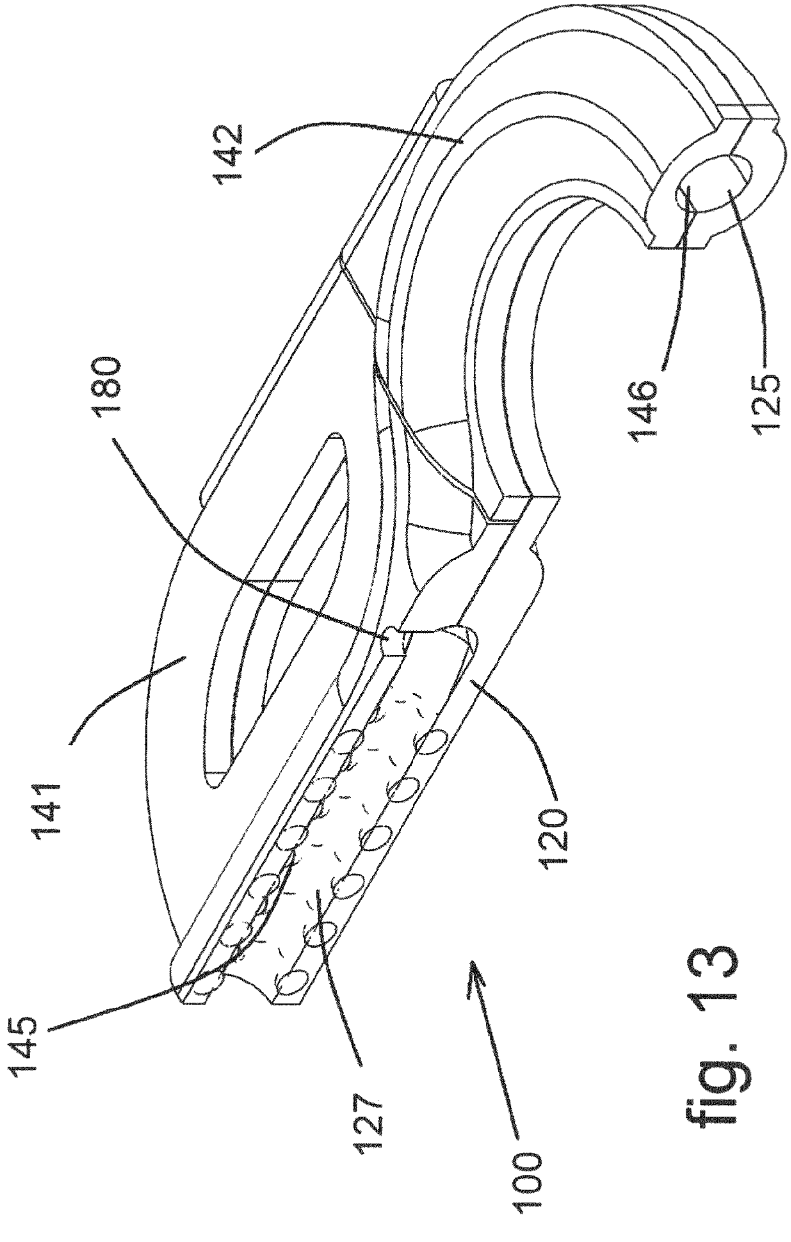
FIG. 13 shows a cross-section of the device of FIG. 12.
Figure 14:
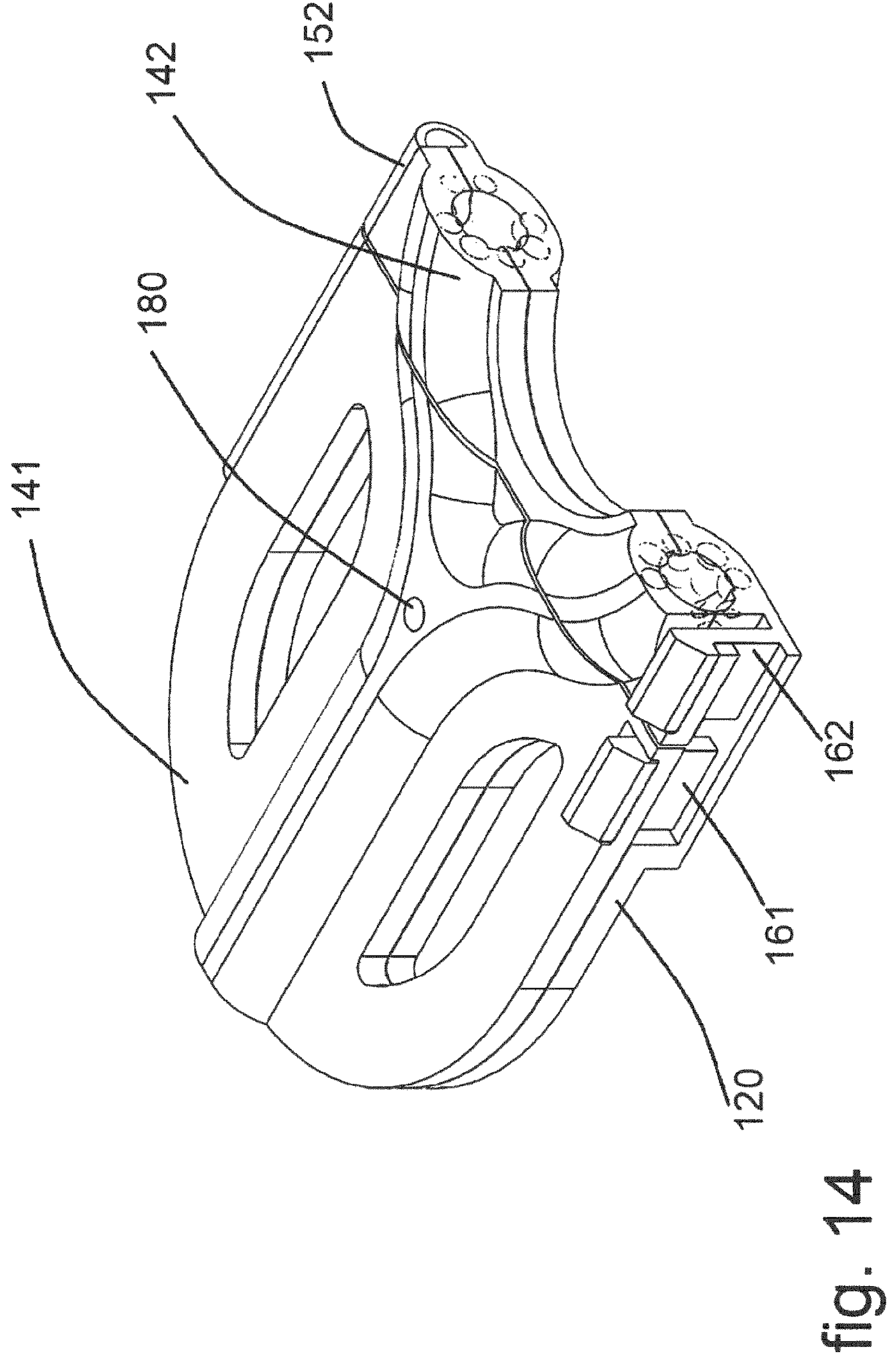
FIG. 14 shows another cross-section of the device of FIG. 12.

With reference to the FIGS. 1-6 an embodiment of an implantable neuroma formation preventing and/or treatment device 1, that is configured to prevent formation of and/or to treat traumatic neuroma at two mammalian nerve stumps, e.g. at the tibial nerve and the peroneal nerve of a human.

The device 1 comprises:

a lower shell member 20, an upper shell member 40.

The lower shell member 20 is provided with:

two open-topped trenches 21, 22, also referred to as first trench 21 and second trench 22, each having a receiving section 21*a*, 22*a* that extends from a respective nerve stump entry port 23, 24 of the device and is configured for placing one mammalian nerve stump therein.

Each trench 21, 22 further has an outlet section 21*b*, 22*b* adjoining the respective receiving section and configured to receive therein nerve fibres projecting from the nerve stump received in the receiving section.

It is illustrated that the trenches 21, 22 are arranged side-by-side, here parallel to one another.

It is illustrated that the device 1 has two nerve stump entry ports 23, 24 at one common side of the device.

The lower shell member 20 further is provided with an open-topped and open-loop shaped third trench 25 having a central region 25*a* and opposed ends 25*b, c* that each adjoin to a corresponding outlet section 21*b*, 22*b*. As the third trench 25, which is open at the top, could also be called an open-topped C-shaped trench 25. The open-loop shaped third trench 25 is configured to install therein an axonal guiding structure having opposed axon entry faces and being configured to allow for entry of regenerating axons from each outlet section via the respective axon entry face into the axonal guiding structure. For example, the axonal guiding structure is an autograft.

The upper shell member 40 is configured to be secured onto the lower shell member 20 after placing of each of the mammalian nerve stumps, e.g. of the tibial nerve and the peroneal nerve of a human, in the respective one of the receiving sections 21*a*, 22*a* and after the installation of the axonal guiding structure in the open-loop shaped third trench 25, so that the secured upper and lower shell members 20, 40 form a closed shell around the nerve stumps and the axonal guiding structure.

It is illustrated here, that the lower shell member 20 and the upper shell member 40 are each of unitary design. When in closed condition, the upper shell member 40 lies over the trenches in the lower shell member.

It is illustrated, as preferred, that the lower shell member 20 has a planar top side relative to which the trenches are recessed, like an open-topped groove, and the upper shell member 40 has a planar lower side with the trenches being recessed in the upper shell member relative to this planar lower side.

It is illustrated here, that the upper shell member 40 and lower shell member 20 are interconnected via a hinge structure 51, e.g. embodied as a living hinge.

It is illustrated that the device 1 can be made as a unitary structure in its entirety, e.g. injection molded, printed, etc.

It is illustrated, that the upper shell member 40 is provided on its lower side, facing the lower shell member 20 when the shell is closed, with three trenches 45, 46, 47 mating with the first, second, and third trenches 12, 22, 25 of the lower shell member 20 respectively, so that—in use—the nerve stumps and the axonal guiding structure are received, seen in cross-sectional view of the composite trench, in part in the trench of the lower shell member 20 and in part in the trench of the upper shell member 40.

The dimensions of the trenches, here of the composite trenches defined by the lower and upper shell member together in closed condition, are, preferably, chosen in correspondence with relevant anatomical dimensions, e.g. of the cross-section, of the nerve stumps to be treated, e.g. so as to achieve a fit between the nerve stump and the (composite) trench. As explained, ahead of installing the nerve stump in the trench, some adhesive, e.g. fibrin glue, can be deposited in the first and second trenches 21, 22 of the lower shell member 20 to enhanced retention of the nerve stump. It is preferred, that no suture is used to retain the nerve stump relative to the device 1.

In an embodiment, the two open-topped first and second trenches 21, 22 in the lower shell member 20 have different cross-sectional areas, e.g. one open-topped trench being configured to receive therein the stump at the peroneal nerve of a human having a first cross-sectional area and the other open-topped trench being configured to receive therein the stump at the tibial nerve of a human having a second cross-sectional area that is greater than the first cross-sectional area. Herein, the nerve stumps can initially protrude from the upper side of the lower shell member, with the remainder of the nerve stumps being received in the mating trenches of the upper shell member. In another embodiment, as shown, these first and second trenches of the lower shell member have similar dimensions.

In an embodiment, the two open-topped first and second trenches 21, 22 have different depths relative to a top surface 20*a* of the lower shell member 20, e.g. one open-topped trench being configured to receive therein the stump at the peroneal nerve of a human having a first depth and the other open-topped trench being configured to receive therein the stump at the tibial nerve of a human having a second depth that is greater than the first depth. Herein, the nerve stumps can initially protrude from the upper side of the lower shell member 20, with the remainder of the nerve stumps being received in the mating trenches of the upper shell member.

The trenches 21, 22, and 25 of at least the lower shell member 120, here also of upper shell member 140, have trench walls embodied at least in one or more zones thereof with retention enhancing formations, e.g. indicated with reference numerals 27, 28 in a zone of sections 21*a*, 22*a* of the first and second trenches 21, 22 and the ends of third trench 25, e.g. bumps, ribs, etc.

The retention enhancing formations in one or more zones 27, 28 of the trenches 21, 22 counteract any loosening of the nerve stumps from the closed device 1, e.g. in conjunction with the application of an adhesive in said zones 27, 28 so that the formations enhance the grip of the glue on the device 1.

The formations 27, 28 in one or more zones of the third trench 25 for the axonal guiding structure counteract any undue shifting of this structure, e.g. when closing the shell or at a later stage, e.g. said retention being enhanced by the application of an adhesive in said one or more zones.

In embodiments, the closing of the shell of device 100 causes a clamping of the nerve stumps that enhances the retention thereof.

As explained herein, in embodiments, one or both of the lower and upper shell members 20, 40 is made of, e.g. molded or printed, biocompatible and/or biodegradable and/or bio-absorbable material.

It is illustrated here, that the lower and upper shell members 20, 40 are provided with cooperating snap lock formations configured to keep the shell closed. It is shown that a snap-type hook 61 is integral with one of the shell members, here lower shell member, whilst the other shell member is provided with cooperating faces 63 behind which the hook 61 snaps when closing the shell.

It is illustrated here, that both the lower and upper shell members 20, 40, are provided remote from the trenches thereof with one or more suture passages 70, 71, 72 therein that are configured to allow for passing a suture there through to stabilize the location of the shell member(s) relative to the mammal, e.g. to the human leg, e.g. prior to installation of the nerve stumps in the trenches and/or after closing the shell upon completion of the installation.

In practical use of the device 1, the following method may be performed:

- the lower shell 20 is placed in proximity of the nerve stumps with the trenches of the lower shell exposed, preferably facing upwards,
- the nerve stumps are each placed via the open top into the first and second trench 21, 22 respectively, e.g. after adhesive being deposited in the first and second trench,
- the axonal guiding structure, e.g. autograft, is placed via the open top into the open-loop shaped third trench 25, e.g. after adhesive being deposited in this third trench,
- the upper shell member 40 is secured onto the lower shell member 20, e.g. both after placing of each of the mammalian nerve stumps in the receiving section 21*a*, 22*a* and after the installation of the axonal guiding structure in the open-loop shaped trench 25, so that the secured upper and lower shell members form a closed shell around the nerve stumps and the axonal guiding structure.

Herein, the nerve stumps can initially protrude from the upper side of the lower shell member, with the remainder of the nerve stumps being received in the mating trenches of the upper shell member.

With reference to FIGS. 7-14 an exemplary embodiment of an implantable neuroma formation preventing and/or treatment device 100 that is configured to prevent formation of traumatic neuroma at one mammalian nerve stump, e.g. of a human, will be discussed.

Generally, the device 100 comprises a lower shell member 120 and an upper shell member 140.

The lower shell member 120 is provided with a single open-topped Y-shaped trench 121 having a receiving section 121*a* that extends from a nerve stump entry port 122 of the device 100 and is configured for placing one mammalian nerve stump therein.

The Y-shaped trench 121 further has branching outlet sections 121*b, c* adjoining the receiving section 121*a* and each configured to receive therein nerve fibres projecting, e.g. as a bundle, from the nerve stump received in the receiving section 121*a*.

The lower shell member 120 is also provided with a single open-topped and open-loop shaped trench 125 having a central region 125*a* and having opposed ends 125*b, c* that each adjoin to a corresponding outlet section 121*b, c*.

The open-loop shaped trench 125 is configured to install therein an axonal guiding structure (not shown), e.g. an autograft, e.g. as discussed in the referenced scientific article, which structure has opposed axon entry faces and is configured to allow for entry of regenerating axons from each outlet section via the respective axon entry face into the axonal guiding structure.

As follows from the FIGS. 7-14, the upper shell member 140, here composed of the parts 141, 142, is configured to be secured onto the lower shell member 120 after placing of the mammalian nerve stump in the receiving section 121*a* and after the installation of the axonal guiding structure in the open-loop shaped trench 125, so that the secured upper and lower shell members 120, 140 form a closed shell about the nerve stump and the axonal guiding structure.

It is illustrated here, that the lower shell member 120 is of unitary design and the upper shell member is composed of two independently movable upper shell member parts 141, 142 in side-by-side arrangement. Each upper shell member part is configured to be secured on a respective portion of the lower shell 120.

For example, one upper shell member part 142 is embodied to overlie the trench 125 with the axonal guiding structure and another upper shell member part 141 being embodied to overlie the trench 121 of the device 100.

It is illustrated here, that the upper shell member parts 141, 142 and lower shell member 120 are interconnected via respective hinge structures 151, 152, e.g. each embodied as a living hinge.

It is illustrated, that the upper shell 140, here parts 141, 142, is provided on its lower side, facing the lower shell member 120 when the shell is closed, with trenches 145, 146 mating with the trenches 121, 125 of the lower shell member 120 respectively, so that—in use—the nerve stump and the axonal guiding structure are received, seen in cross-sectional view of the composite trench, in part in the trench of the lower shell member 120 and in part in the trench of the upper shell member 141, 142.

The dimensions of the trench, here the composite trench formed by trenches 121 and 145, are, preferably, chosen in correspondence with relevant anatomical dimensions, e.g. of the cross-section, of the nerve stump to be treated, e.g. so as to achieve a fit between the nerve stump and the (composite) trench. As explained, ahead of installing the nerve stump in the trench, some adhesive, e.g. fibrin glue, can be deposited in the trench 125 of the lower shell member 120 to enhanced retention of the nerve stump. It is preferred, that no suture is used to retain the nerve stump relative to the device 100. Herein, the nerve stump can initially protrude from the upper side of the lower shell member, with the remainder of the nerve stump being received in the mating trench of the upper shell member.

The trenches of at least the lower shell member 120, here also of upper shell member 140, have trench walls embodied at least in one or more zones thereof with retention enhancing formations, e.g. indicated with reference numerals 127 in a zone of section 121*a* and 128 *a, b* in zones of the trench 125, 146.

The formations in one or more zones 127 of trench 121, 145 counteract any loosening of the nerve stump from the closed device 100, e.g. in conjunction with the application of an adhesive in said zone 127 so that the formations enhance the grip of the glue on the device 100.

The formations in one or more zones 128*a, b* of the trench 125, 146 for the axonal guiding structure counteract any undue shifting of this structure, e.g. when closing the shell or at a later stage, e.g. said retention being enhanced by the application of an adhesive in said one or more zones.

In embodiments, the closing of the shell of device 100 causes a clamping of the nerve stump that enhances the retention thereof.

As explained herein, in embodiments, one or both of the lower and upper shell members 120, 140 is made of, e.g. molded or printed, biocompatible and/or biodegradable and/or bio-absorbable material.

It is illustrated here, that the lower and upper shell members 120, 140, here parts 141, 142, are provided with cooperating snap lock formations configured to keep the shell closed. It is shown that one or more, here two, snap-type hooks 161, 162 are integral with one of the shell members, here lower shell member, whilst the other shell member is provided with cooperating faces 163, 164 behind which the hooks 161, 162 the hooks snap when closing the shell.

It is illustrated here, that both the lower and upper shell members 120, 140, are provided remote from the trenches thereof with one or more suture passages 170*a, b*, 171*a, b*, 172*a, b* therein that are configured to allow for passing a suture there through to stabilize the location of the shell member(s) relative to the mammal, e.g. to the human leg, e.g. prior to installation of the nerve stump(s) in the trench(es) and/or after closing the shell upon completion of the installation.

It is illustrated here, that the upper shell member 141 is provided with at least one injection port 180, which injection port 180 is distinct from the nerve entry port of the device 100 and is configured for introduction of a fluid, e.g. a saline solution or an adhesive, into the closed shell 100 by means of a syringe.

In practical use of the device 100, the following method may be performed:

- the lower shell 120 is placed in proximity of the nerve stump with the trenches 121, 125, of the lower shell exposed, preferably facing upwards,
- the nerve stump is placed via the open top into the trench 121, e.g. after adhesive being deposited in the trench 121,
- the axonal guiding structure, e.g. an autograft, is placed via the open top into the open-loop shaped trench 125, e.g. after adhesive being deposited in this trench 125,
- the upper shell, here with parts 141, 142, is secured onto the lower shell member, e.g. both after placing of the mammalian nerve stump in the receiving section 121*a* and after the installation of the axonal guiding structure in the open-loop shaped trench 125, so that the secured upper and lower shell members form a closed shell about the nerve stump and the axonal guiding structure.

If desired, for example, the device 100 also allows for an approach wherein one first secures the part 141 onto the lower shell member 120 directly following the installation of the nerve stump and then installs the axonal guiding structure followed by closing of the part 142 onto the lower shell member 120.

As the upper shell is provided with an injection port 180 that is located in proximity of the join between the outlet section of a nerve stump receiving trench on the one hand and the end of axons guide receiving open-loop shaped trench, it is envisaged that in a practical use of the device 100—once the shell is closed—first a solution, e.g. a saline solution is injected into the closed shell via the port 180, e.g. to fill the space between the nerve stump and the axonal guiding structure. Then, in embodiments, the port 180 is the plugged, e.g. by injecting adhesive into the port 180.

Figure 15:
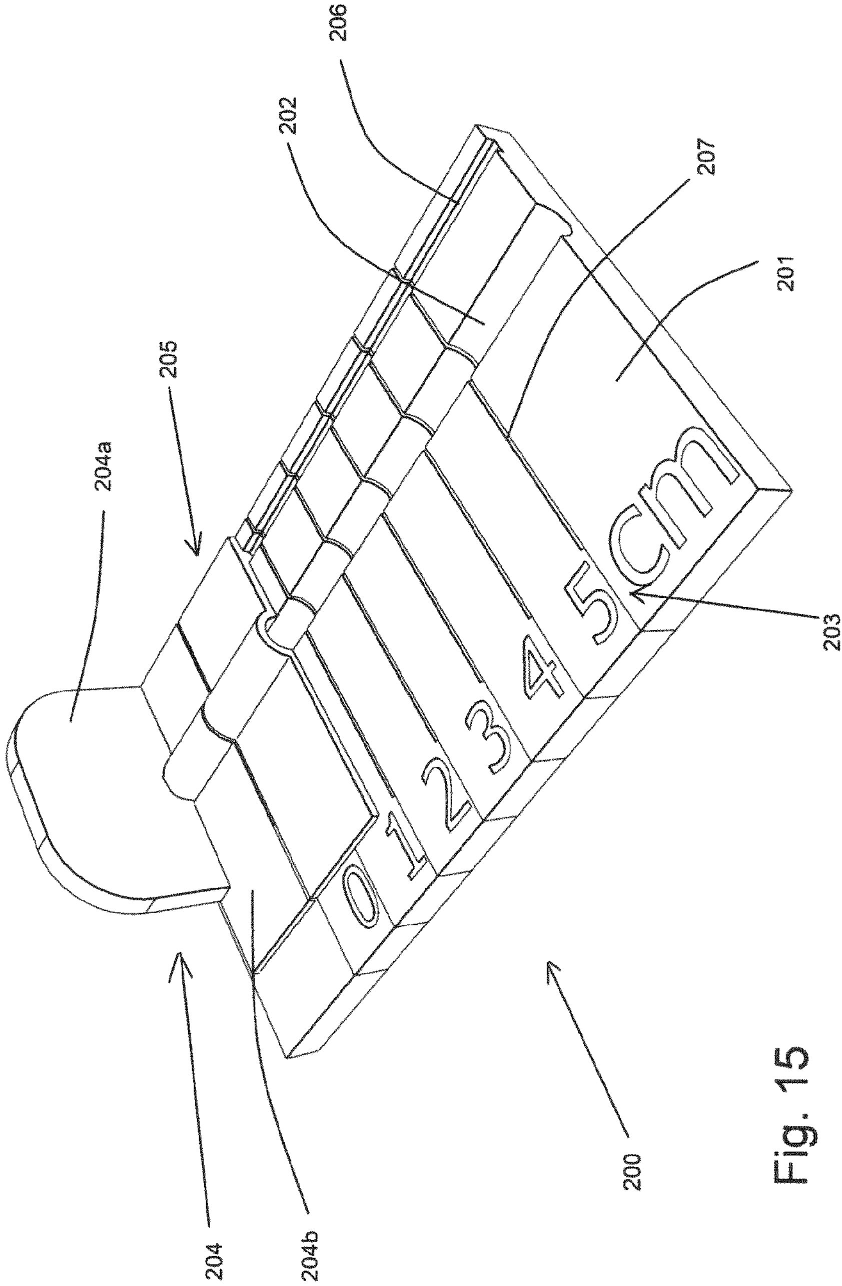
FIG. 15 shows a nerve graft preparation tool of the invention, e.g. as part of a kit together with one or more of the devices as discussed herein.

FIG. 15 shows an example of an inventive graft preparation tool 200 that is configured to assist in cutting to length a nerve graft, in practice an autograft. For example, the graft is to be received in the axonal guiding structure trench of one of the devices discussed herein, or for other situations where a nerve graft of a predetermined length is desired.

Generally, the preparation tool 200 is configured to receive an autograft, e.g. an autograft, e.g. taken from the amputated part of the leg or other limb. The tool 200 provides an indication of the length as well as a guide for a surgical knife so as to achieve a cutting of the nerve graft to the predetermined length.

The tool 200 comprises a board 201, e.g. of plastic, on which the nerve graft is to be laid and generally serves as a cutting board.

The board 201 is provided with a linear receiver, here a trench 202, in which the nerve graft to be made to length is placed. As preferred, the trench 202 has a depth that is smaller than the diameter of the nerve graft, so that the nerve graft protrudes somewhat above the board top surface adjacent the trench 202.

Along the length of the trench 202 the board 201 is provided with indicia forming a ruler 203 allowing to visualize position(s) where the nerve graft is to be severed in order to obtain the desired length, e.g. corresponding to the design of the devices discussed herein.

In the embodiment shown, the ruler 203 has indications representing centimetres. In embodiments, or in combination herewith, the ruler 203 could have indications representing a length matching the length of the graft to be placed in one or both of the devices as discussed herein.

As nerve grafts are commonly slippery and difficult to grasp and retain by hand, the tool 200, as preferred, is provided with at least one graft retainer member, here two members 204, 205 that can retain the graft relative to the board 201, e.g. clamp the graft on the board. For example, as shown, at least one retainer member, here both members 204, 205 is configured to be held relative to the board 201 at multiple positions along the length of the nerve receiver, here the trench 202. For example, as shown, at least one retainer member 204 can be fitted onto the board 201 and over the nerve graft already placed in the receiver 202 at various positions along the length of the nerve receiver 202. For example, as shown, the board 200 is provided with one or more elongated snap-fit formations, e.g. a groove 206 (as shown) and/or a slit and/or a rail, extending along the length of the receiver 202, which can cooperate with one or more snap-fit formations on the retainer member 204, here a stud fitting into the groove. In another embodiment, at least one retainer member 204, 205 is slidably held on the board so as to be slidable along the length of the nerve receiver.

As illustrated, the at least one retainer member 204, 205 may have at is underside a recess mating with the trench 202 to accommodate the portion of the nerve graft that projects above the trench 202, e.g. to avoid undue local squeezing to the graft.

Preferably, the tool 200 is provided with two graft retainer members 204, 205, allowing to retain the nerve graft at two locations along the length thereof ahead of severing the graft at one or two locations, e.g. in proximity to one or both of the retainer members 204, 205.

For example, as shown, at least one retainer member 204, 205 equally serves as a guide for a surgical knife when severing the graft, e.g. the retainer member 204, 205 having a side perpendicular to the receiver 202 along which the knife can be moved during the severing.

FIG. 15 illustrates that retainer member 204 is provided with a vertical knife guide plate portion 204*a* that projects from a horizontal base portion 204*b* of the member 204 along a side that is perpendicular to the receiver 202. In use, the portion 204*a* provides for enhanced guidance of the knife. The member 205 may be of the same design.

FIG. 15 also illustrates that the board 201 may be provided with parallel knife guide formations, here grooves 207, that are perpendicular to the receiver 202, e.g. at positions corresponding to likely cuts of the nerve graft. These formations, here grooves 207 extend at both sides of the receiver 202, here also across the receiver, and serve to guide the point of the knife while making the cut. The grooves 207 may be shallow for this purpose, e.g. of a lesser depth than the trench 202.

In embodiments, the tool 200 is disposable, so for single use only.

In embodiments, the tool 200 is distributed, e.g. packaged, in combination with one of the devices discussed herein, e.g. the board 201 having a ruler 203 and/or parallel knife guide formations, here grooves 207, tuned to the length of the graft that is to be placed in the device.

The invention claimed is:

1. An implantable neuroma formation preventing and/or treatment device configured to prevent formation of and/or to treat traumatic neuroma at two mammalian nerve stumps, the device comprising:

a lower shell member, an upper shell member, wherein the lower shell member is provided with:

open-topped first and second trenches, each having a receiving section that extends from a respective nerve stump entry port of the device and is configured for placing one mammalian nerve stump therein, wherein each first trench and second trench further has an outlet section adjoining said receiving section and configured to receive therein nerve fibres projecting from the nerve stump received in the receiving section, an open-topped and open-loop shaped third trench having opposed ends that each adjoin to a corresponding outlet section of the first and second trenches, the third trench being configured to install therein an axonal guiding structure having opposed axon entry faces and being configured to allow for entry of regenerating axons from each outlet section via the respective axon entry face into the axonal guiding structure, wherein the upper shell member is configured to be secured onto the lower shell member after placing of each of the mammalian nerve stumps in the respective one of the receiving sections and after the installation of the axonal guiding structure in the third trench, so that the secured upper and lower shell members form a closed shell about the nerve stumps and the axonal guiding structure.

2. The implantable device according to claim 1, wherein the first and second trenches have different cross-sectional areas, the first trench being configured to receive therein the stump at the peroneal nerve of a human having a first cross-sectional area and the second trench being configured to receive therein the stump at the tibial nerve of a human having a second cross-sectional area that is greater than the first cross-sectional area.

3. The implantable device according to claim 1, wherein the first and second trenches have different depths relative to a top surface of the lower shell member, the first trench being configured to receive therein the stump at the peroneal nerve of a human having a first depth and the second trench being configured to receive therein the stump at the tibial nerve of a human having a second depth that is greater than the first depth.

4. The implantable device according claim 1, wherein the upper shell is provided on its lower side, facing the lower shell when the shell is closed, with trenches mating with the trenches of the lower shell, so that—in use—the at least one nerve stump and the axonal guiding structure are received, seen in a cross-sectional view, in part in the trench of the lower shell and in part in the trench of the upper shell.

5. The implantable device according to claim 1, wherein the secured upper and lower shell members form a closed shell about the at least one nerve stump and the axonal guiding structure and causes a clamping of the at least one nerve stumps.

6. The implantable device according to claim 1, wherein the lower shell member is a unitary lower shell member.

7. The implantable device according to claim 1, wherein the upper shell member is a unitary upper shell member, e.g. molded or printed, e.g. of biocompatible and/or biodegradable and/or bio absorbable material.

8. The implantable device according to claim 1, wherein the upper shell member and lower shell member are interconnected via a hinge structure.

9. The implantable device according to claim 1, wherein the lower and upper shell members are provided with cooperating snap formations configured to keep the shell closed.

10. The implantable device according to claim 1, wherein both the lower and upper shell member are provided remote from the trenches thereof with one or more suture passages therein that are configured to allow for passing a suture there through to stabilize the location of the shell members relative to the mammal.

11. The implantable device according to claim 1, wherein at least one of the lower shell member and the upper shell member, is provided with at least one injection port, each injection port being distinct from the one or two nerve entry ports of the device and being configured for introduction of a fluid into the closed shell by means of a syringe.

12. The implantable device according to claim 1, wherein the trenches of the lower shell have trench walls embodied at least in one or more zones thereof with retention enhancing formations, provide enhanced retention of the nerve stump or axonal guiding structure.

13. A method to prevent formation of and/or to treat traumatic neuroma at two mammalian nerve stumps, wherein use is made of an implantable device according to claim 1.

14. The method according to claim 13, wherein:

the lower shell is placed in proximity of two mammalian nerve stumps with the trenches of the lower shell exposed, the nerve stumps are placed via the open top into the respective first and second trench, an axonal guiding structure is placed via the open top into the open-loop shaped trench, the upper shell is secured onto the lower shell member after placing of each of the two mammalian nerve stumps in the respective one of the receiving sections and after the installation of the axonal guiding structure in the open-loop shaped trench, so that the secured upper and lower shell members form a closed shell about the two nerve stumps and the axonal guiding structure.

15. The method according to claim 14, wherein the upper shell is provided with at least two injection ports, each located in proximity of a respective join between the outlet section of a nerve stump receiving trench on the one hand and the axonal guiding structure receiving trench, and wherein the method involves injecting a fluid via the injection port into a space between the nerve stump and the axonal guiding structure.

16. An implantable neuroma formation preventing and/or treatment device configured to prevent formation of and/or to treat traumatic neuroma at a mammalian nerve stump, the device comprising:

a lower shell member, an upper shell member, wherein the lower shell member is provided with:

an open-topped Y-shaped trench having a receiving section that extends from a nerve stump entry port of the device and is configured for placing one mammalian nerve stump therein, wherein the Y-shaped trench further has branching outlet sections adjoining said receiving section and each configured to receive therein nerve fibres projecting from the nerve stump received in the receiving section, an open-topped and open-loop shaped trench having opposed ends that each adjoin to a corresponding outlet section, the open-loop shaped trench being configured to install therein an axonal guiding structure having opposed axon entry faces and being configured to allow for entry of regenerating axons from each outlet section via the respective axon entry face into the axonal guiding structure, wherein the upper shell member is configured to be secured onto the lower shell member after placing of the mammalian nerve stump in the receiving section and after the installation of the axonal guiding structure in the open-loop shaped trench, so that the secured upper and lower shell members form a closed shell about the nerve stump and the axonal guiding structure.

17. A method to prevent formation of and/or to treat traumatic neuroma at one mammalian nerve stump, wherein use is made of an implantable device according to claim 16.

18. The method according to claim 17, wherein:

the lower shell is placed in proximity of the mammalian nerve stump with the trench of the lower shell exposed, the nerve stump is placed via the open top into the trench, the axonal guiding structure is placed via the open top into the open-loop shaped trench, the upper shell is secured onto the lower shell member after placing the mammalian nerve stump in the receiving section and after the installation of the axonal guiding structure in the open-loop shaped trench, so that the secured upper and lower shell members form a closed shell about the nerve stump and the axonal guiding structure.

19. The method according to claim 18, wherein the upper shell is provided with an injection port that is located in proximity of a join between the outlet section of the nerve stump receiving trench on the one hand and the axons guiding structure receiving trench, wherein the method involves injecting a fluid via the injection port into the space between the nerve stump and the axonal guiding structure.

* * * * *